United States Patent [19]

Doeding et al.

[11] Patent Number: 4,788,152
[45] Date of Patent: Nov. 29, 1988

[54] APPARATUS FOR DETERMINING COAGULATION PARAMETER

[75] Inventors: Jürgen Doeding, Bensheim; Hans Wielinger, Langgewann; Rolf Lerch, Ilvesheim, all of Fed. Rep. of Germany

[73] Assignee: Boehringer Mannheim GmbH, Mannheim, Fed. Rep. of Germany

[21] Appl. No.: 27,628

[22] Filed: Mar. 19, 1987

[30] Foreign Application Priority Data

Mar. 27, 1986 [DE] Fed. Rep. of Germany ....... 3610429

[51] Int. Cl.$^4$ .............................................. G01N 1/18
[52] U.S. Cl. ...................................... 436/69; 436/170; 436/178
[58] Field of Search ................. 436/69, 170, 177, 178; 422/55–58; 210/508, 509, 679; 435/13

[56] References Cited

U.S. PATENT DOCUMENTS

| 4,144,306 | 3/1979 | Figueras | 422/56 |
| 4,475,575 | 10/1984 | Vogel et al. | 210/509 |
| 4,620,932 | 11/1986 | Howery | 210/508 |

FOREIGN PATENT DOCUMENTS

| 162302 | 11/1985 | European Pat. Off. | 422/56 |
| 162301 | 11/1985 | European Pat. Off. | 422/56 |
| 3237233 | 2/1984 | Fed. Rep. of Germany | 422/56 |
| 139067 | 8/1983 | Japan | 422/56 |

Primary Examiner—Benoît Castel
Attorney, Agent, or Firm—Felfe & Lynch

[57] ABSTRACT

The present invention provides a test carrier for the determination of coagulation parameters, wherein it includes a test layer which contains silanized glass fibres which are coated with polyvinyl alcohol or polyvinyl alcohol/vinyl acetate.

7 Claims, 1 Drawing Sheet

APPARATUS FOR DETERMINING COAGULATION PARAMETER

BACKGROUND OF THE INVENTION

The present invention is concerned with a test carrier for the determination of so-called coagulation parameters, i.e. for the analysis of blood with regard to the components influencing the coagulation process.

For the quantitative and qualitative analytical determination of components of body fluids, especially of blood, so-called carrier-bound tests have recently been increasingly used. In these, reagents are embedded in appropriate layers of a solid test carrier which is brought into contact with the sample. The reaction of sample and reagents leads to a detectable signal, especially to a colour change, which can be evaluated visually or with the help of an apparatus, usually by reflection photometry.

Test carriers are frequently constructed as test strips which consist essentially of a longitudinal carrier layer of synthetic resin material and test fields applied thereon. However, test carriers are also known in the form of quadratic or rectangular platelets.

U.S. Pat. No. 4,477,575 describes agents and processes for the separation of plasma or serum from whole blood and especially test carriers for the diagnostic determination of components of body fluids (so-called parameters) which make it possible to determine component materials of whole blood in a simple manner. According to this patent specification, the plasma can be separated from the erythrocytes by allowing the whole blood to run through a layer of glass fibres with fibre diameters of less than 2.5 μm which hold back the erythrocytes. The blood is preferably applied to one end of a rectangular glass fibre fleece from which the plasma is transported by capillary forces into the other region of the device. After the plasma-obtaining procedure, this fleece part filled with plasma is pressed against a matrix (paper, absorbent films or the like) containing the necessary reagents in which matrix is carried out the detection reaction for the parameter to be detected via remission measurements.

This simple plasma obtaining and plasma transport system can be used for all important clinical-chemical parameters with the exception of parameters which are to be determined involving haemostasiological determination. It is known that, in principle, coagulation analyses are to be carried out in synthetic resin or glass vessels which are inactivated by a coating of silicone resin because untreated glass influences the coagulatability of blood and plasma. Thus, due to activation, glass shortens the Quick one-phase coagulation time of plasmas, the coagulation factors of which lie within the normal range. In the case of lower percentage plasmas, the Quick one-phase coagulation time is prolonged due to inactivation of coagulation factors. In particular, glass inactivates Factors V and IIa. Due to this inactivation and thus falsely prolonged coagulation times, the diagnostic usefulness is destroyed because the ratios of the individual coagulation factors are displaced. The Quick value, given as a percentage, includes, besides the fibrinogen concentration, the activity of Factors II, V, VII and X. A pool plasma from healthy donors is defined as 100% plasma and, by means of dilution with physiological saline, appropriate lower percentage plasmas are prepared. By means of this dilution series, a reference curve is produced on the basis of which are determined the Quick values for patients' plasmas.

However, the partial thromboplastin time (PTT) is also negatively influenced by inactivation of Factors XII and XI. The detection of antithrombin III and heparin is considerably disturbed due to inactivation of thrombin by glass.

SUMMARY OF THE INVENTION

Therefore, it is an object of the present invention to provide glass fibre layers which are especially useful as a separation and transport system in test carriers, said glass fibre layers being coagulation-neutral and thereby being usable for haemostasiological investigations. They retain their separation and transport properties.

Thus, according to the present invention, there is provided a test carrier for the determination of coagulation parameters, which includes a test layer which contains glass fibres which are coated with polyvinyl alcohol or polyvinyl alcohol/vinyl acetate.

We have found that glass surfaces can be so modified by the addition of polyvinyl alcohols so that they retain the hydrophilic properties which are necessary, for example, for the absorbency of glass fibre fleeces but lose their influence on the coagulation factors, i.e. become coagulation-neutral. This is especially surprising because it is known that glasses can be superficially coated by siliconization with silicone resin emulsions. This eliminates influence on coagulation factors but siliconisation, in the special case of glass fibres, brings about such a high degree of hydrophobicity of the surfaces that wetting can no longer take place and thus the fibres completely lose their plasma transport properties and erythrocyte-separation properties.

Polyvinyl alcohol is produced from polyvinyl acetate by saponification. Depending upon the properties which the product should have, one carries out either partial or complete saponification of the acetate. For use according to the present invention, there can be employed not only a completely saponified product but also a partly saponified product. Polyvinyl alcohols, which are commercially available in large amounts, differ especially with regard to their average molecular weight, which is normally from about 10,000 to 100,000 and, in some special cases, can also have considerably higher values, and with regard to the residual content of acetyl radicals. The lower molecular weight compounds, which contain about 5 to 15% and especially about 10% of acetyl radicals, are the most easily soluble in water, whereas high molecular weight products and/or products with a higher content of acetyl radicals are less soluble in water. The interaction of polyvinyl alcohol chains with one another also has an influence on the solubility. Due to a partial parallel orientation of the polymer chains, in certain regions "crystalline zones" arise. The more regular the polymer chains are constructed, the greater the tendency toward parallel orientation Similarly, as the proportion of acetyl radicals lowers, parallel orientation increases as these radicals counter parallel orientation strongly. Therefore, in the case of a degree of saponification of 97 to 100%, i.e. in the case of a degree of acetylation of 3 to 0%, the "crystallinity" increases especially strongly, whereas, on the other hand, the cold water solubility decreases strongly.

Furthermore, the water solubility can be reduced by post-treatment with aldehydes (acetalization) or by other chemical changes of the alcohol groups. The polyvinyl alcohols with a low cold water solubility but with a good solubility in warm water are especially useful according to the present invention. At 20° C., the products should dissolve in water only slowly or not at all but at temperatures of from 50° to 100° C. and especially at temperatures above 60° C. should dissolve easily in water.

The glass fibre fleeces according to the present invention can be produced by treating an appropriate glass fibre fleece with a solution of polyvinyl alcohol in water or an appropriate organic solvent and subsequently drying, preferably at a temperature above 60° C. and more preferably at a temperature of from 90° to 140° C., or by adding polyvinyl alcohol in the course of producing the glass fibre fleece. As is known, glass fibre fleeces are produced by suspending dried and felted glass fibres, which have an average diameter of from 0.1 to 20 $\mu$m and a length of from 0.1 to 5 mm., in a very large excess of water to produce a pulp. This pulp is divided up and shaped into thin layers analogously to the processes conventionally used in paper making, using conventional paper-making machines and then dried. The polyvinyl alcohol powder or fibres added to the pulp is uniformly distributed in the mass during the slurrying of the glass fibres and, in the subsequent production of the fleece, dissolved or melted to such an extent that, subsequent to the drying of the fleece, a uniform coating is formed on the glass fibres. This coating results in the glass fibres becoming coagulation-neutral but, on the other hand, possessing hydrophilic properties to such an extent that the absorbency and the transport of water or of aqueous solutions by this fleece is not impaired.

Silanized glass fibres are especially preferably added to the pulp. Suitable fibres of this kind are described in co-pending U.S. application Ser. No. 021,743. reference hereby being made to the complete content of this patent specification. These are then additionally coated according to the present invention with polyvinyl alcohol or polyvinyl alcohol/vinyl acetate. Glass fibre layers are thereby obtained which, to a large extent, are coagulation-neutral and are characterized by especially good strength.

Since the polyvinyl alcohol coats the glass fibres relatively uniformly when it is applied according to the present invention, even relatively small amounts, especially of from about 0.5 to 20% and preferably of from 1 to 5%, suffice in order to make the fibres coagulation-neutral. Proportions of above 20% would not be harmful to the desired effect but, for economic reasons, are not sensible.

Insofar as the glass fibre fleece are to be used not only for the transport of serum and plasma but also for the separation of erythrocytes from plasma according to U.S. Pat. No. 4,477,575, the glass fibres should have an average diameter of from 0.2 to 5 $\mu$m. and preferably of from 0.5 to 2.5 $\mu$m. and the fleece should have a density of from 0.1 to 0.5 g./cm$^3$. However, insofar as it is only a question of coagulation neutrality and transport properties, glass fibres of greater thickness and fleece of a different density can also be used. In the case of such fleece, the polyvinyl alcohol content of the fleece can also be greater than the otherwise advantageous content of 20%.

The glass fibres according to the present invention are converted by conventional processes into fleece which, as is described, inter alia, in the following Examples, can be used in agents for the determination of coagulation parameters. However, they can also be used in the form of short columns for obtaining plasma according to U.S. Pat. No. 4,477,575 whereafter the plasma can then be used in conventional manner in coagulation tests.

Further possible test carriers according to the present invention for the determination of coagulation parameters can be produced analogously to the agents described in U.S. Pat. No. 4,477,575, to which reference is hereby made. Obviously, in such agents not only the glass fibre layers according to the present invention but also all other parts coming into contact with the plasma must consist of coagulation-neutral materials, in which case, in particular, there are used appropriate, known synthetic resins.

BRIEF DESCRIPTION OF THE DRAWINGS

The present invention is explained in more detail in the following, with reference to the accompanying drawings and several Examples.

DESCRIPTION OF THE PREFERRED EMBODIMENTS

Figure 1:
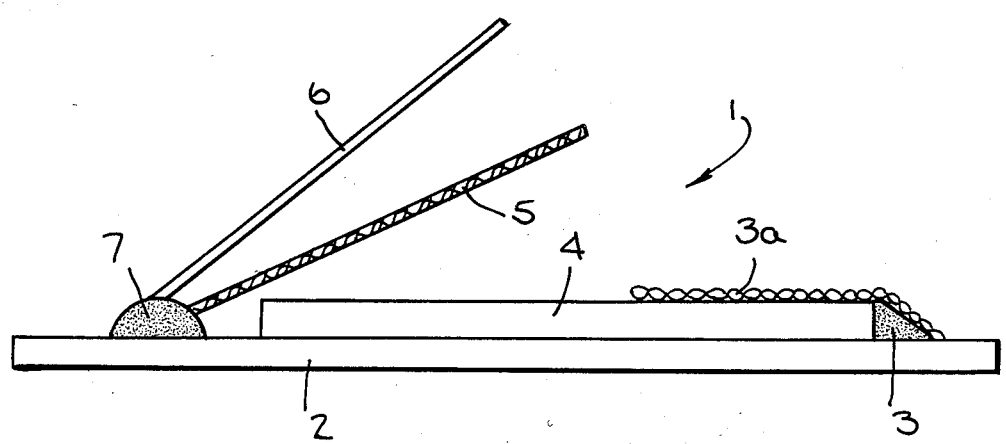
FIG. 1 is a schematic side view of a test carrier according to the present invention.

The test carrier 1 illustrated in FIG. 1 has the principal form of a conventional carrier strip. On to a carrier layer 2 of a synthetic resin film, for example polystyrene, there is fixed, with a melt adhesive strip 3, a glass fibre layer 4 and a covering mesh 3a partly overlapping the glass fibre layer 4.

On the other side, the glass fibre layer 4 is overlapped by an oxidation agent layer 5 and a reaction layer 6 which are fixed flap-like with a further melt adhesive strip 7 to the carrier layer 2.

For carrying out an analysis, a droplet of blood is applied to the covering mesh 3a and transported via the glass fibre layer 4 into the region of the oxidation agent layer 5 and of the reaction layer 6. A separation of the plasma thereby takes place in the manner described in U.S. Pat. No. 4,477,575. In order to initiate the reaction with the reagents contained in the layers 5 and 6, these are pressed downwardly so that the sample liquid penetrates into these layers and the corresponding reactions take place.

Further details regarding the chemical reactions which take place in the case of a coagulation test of the present kind are to be found in European patent specification No. 0,182,373 and in the following Examples.

EXAMPLE 1

Production of a Glass Fibre Fleece According to the Present Invention 1 kg. of glass fibres is slurried with 420 liters of water which has been adjusted to a slightly acidic pH of 3.0 for the isolation of the fibres in a beater. In the storage container of a paper machine dilution is carried out to 0.3% and to this dilution are added 50 g. polyvinyl alcohol fibres (Kuralon VPB 105-2 of the firm Kuraray) and mixed. In the stuff box of the paper machine, the suspension is diluted to 0.05% with the water from the circulation and this applied to the sieve of the paper-making machine, sheet formation here taking place. The sheets are then dried on a drying cylinder at 110° to 120° C. Depending upon the adjustment of the machine, fleece are obtained with a weight per unit surface area of 20 to 100 g./m$^3$ and a thickness of from 0.2 to 1 mm.

EXAMPLE 2

Testing of the Glass Fibre Fleece for Coagulation Neutrality

From the glass fibre fleece produced according to Example 1, samples each of 40 mg. are brought together with 300 μl. amounts of pool plasma from healthy donors and also from patients who have been treated with anticoagulants, followed by incubation for 1 minute at 37° C. Thereafter, the plasmas are separated off by centrifuging. The plasmas are investigated before and after the treatment with the glass fibre fleece for the Quick one-phase coagulation time. The clotting test can thereby be used: starting of the coagulation cascade with calcium chloride and thromboplastin and hooking the sample, the time up to formation of fibrin threads thereby being measured. There can also be used a photometric test for the determination of the Quick time (see U. Becker et al., Neue Aspekte der Gerinnungsdiagnostik, pub. F. K. Schattauer Verlag, Stuttgart and New York, 1984, pp. 17–30).

EXAMPLE 3

Determination of the Quick One-Phase Coagulation Time (a) Production of the test carrier.

A test carrier according to FIG. 1 of the accompanying drawings is produced. The glass fibre layer 4 is a fleece with a weight per unit surface area of 50 to 60 g./m² and a thickness of 0.5 mm. In the longitudinal direction of the test carrier, it has a length of 15 mm. The covering mesh 3a has a thread thickness of 140 μm. and a mesh size of 250 μm.

The reaction layer 6 consists of a polycarbonate film of 200 μm. thickness on to which a reagent film has been raked on in a wet film thickness of 110 μm. and dried at 45° C. The film-forming mass is produced as follows:

In 1 liter of water are dissolved 10 g. of a linear crosslinked polyacrylamide.

100 mmole 4-(2-hydroxyethyl)-1-piperazine-ethanesulphonic acid; 1 mmole Tos-Gly-Pro-Arg-p-phenylenediamine; 15 mmole N-(4-fluorophenyl)-N-methylaminomethane-phosphonic acid and 4.9 g. rabbit brain thromboplastin. This solution is adjusted to a pH of 7.5 with an aqueous solution of sodium hydroxide.

The oxidizing agent layer 5 consists of an appropriately impregnated nylon mesh (filament thickness about 40 μm., mesh size about 60 μm.).

The mesh is impregnated with an aqueous solution of 50 mmole potassium hexacyanoferrate-(III)/liter and 50 mmole calcium chloride/liter.

(b) Comparison between test carriers according to the present invention and those in which normal glass fleece have been used.

Figure 2:
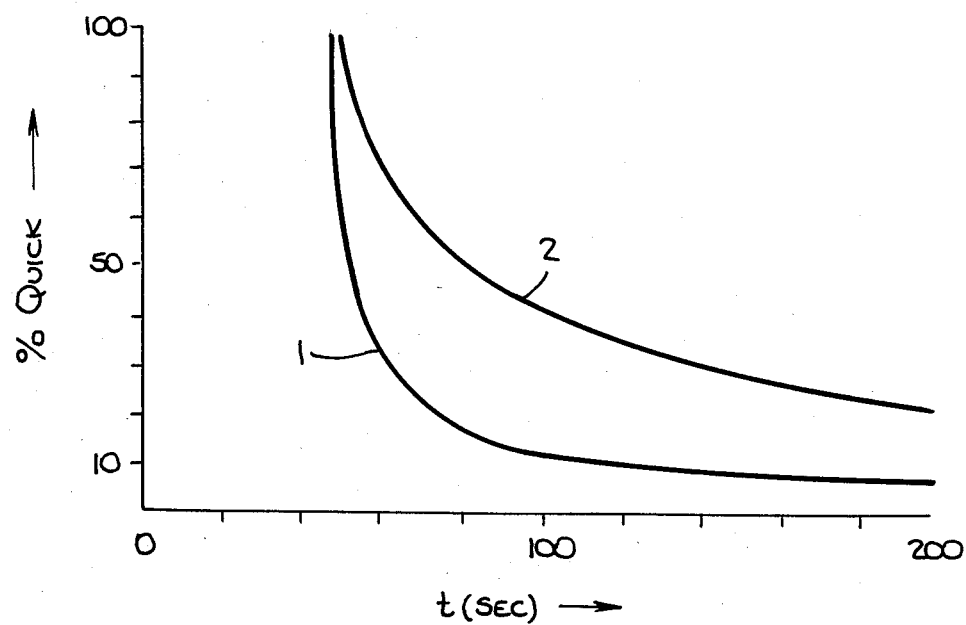
FIG. 2 is a remission curve which was produced with the use of a test carrier according to FIG. 1.

On to the nylon mesh 3a, with which the glass fibre fleece 4 is fixed, are pipetted, in each case, 35 μl. of citrate plasma from a dilution series of 100%, 50%, 33%, 25% and 12.5% in physiological saline. The test carriers are then warmed to 37° C. and the colour formation monitored according to the time with the use of a remission photometer. It is thereby to be observed that, with the glass fibre fleece according to the present invention, substantially higher signals are obtained than with the untreated glass fibre fleece (see FIG. 2 of the accompanying drawings). As Quick time, there is taken the time within which a remission decrease of 10% remission is achieved. The differences are illustrated numerically in the following Table:

TABLE

| plasma | time in seconds for a remission decrease of 10% | |
|---|---|---|
| | with glass fibre fleece according to the invention | with uncoated glass fibre fleece |
| 100% | 44.7 | 46.2 |
| 50% | 51.5 | 78.8 |
| 33% | 58.8 | 121.7 |
| 25% | 66.0 | 160.2 |
| 12.5% | 99.0 | no longer measurable |

While there have been described what are at present considered to be the preferred embodiments of this invention, it will be obvious to one skilled in the art that various changes and modifications may be made therein without departing from the invention, and it is, therefore, aimed to cover all such changes and modifications as fall within the true spirit and scope of the invention.

We claim:

1. Test carrier for determining a coagulation parameter of blood comprising a reagent for determining said parameter and a test layer, said test layer containing silanized glass fibers and a coating layer of polyvinyl alcohol or polyvinyl alcohol/vinyl acetate.

2. Test carrier of claim 1, wherein said test layer contains from 0.5 to 20% polyvinyl alcohol.

3. Test carrier of claim 1, wherein said test layer contains from 1 to 5% polyvinyl alcohol.

4. Test carrier of claim 1, wherein said glass fibers have an average diameter of from 0.2 to 5 μm.

5. Test carrier of claim 1, wherein said glass fibers have a density of from 0.1 to 0.5 g/cm³.

6. Test carrier of claim 1, wherein said glass fibers have an average diameter of from 0.2 to 0.5 μm and said test layer has a density of from 0.1 to 0.5 g/cm³.

7. Test carrier of claim 1, wherein said test layer is a fleece.

* * * * *